United States Patent [19]

Wetterich et al.

[11] Patent Number: 6,090,853
[45] Date of Patent: Jul. 18, 2000

[54] FUNGICIDALLY ACTIVE CARBOXYLIC ACID AMIDES

[75] Inventors: Frank Wetterich, Mutterstadt; Oliver Wagner, Bexbach; Karl Eicken, Wachenheim; Eberhard Ammermann, Heppenheim; Siegfried Strathmann, Limburgerhof; Gisela Lorenz, Hambach; John-Bryan Speakman, Bobenheim, all of Germany

[73] Assignee: BASF Aktiengesellschaft, Ludwigshaften, Germany

[21] Appl. No.: 09/155,099

[22] PCT Filed: Mar. 7, 1997

[86] PCT No.: PCT/EP97/01161

§ 371 Date: Sep. 21, 1998

§ 102(e) Date: Sep. 21, 1998

[87] PCT Pub. No.: WO97/35838

PCT Pub. Date: Oct. 2, 1997

[30] Foreign Application Priority Data

Mar. 22, 1996 [DE] Germany ............... 196 11 350

[51] Int. Cl.[7] .................. A01N 37/18; C07C 233/58
[52] U.S. Cl. .................. 514/623; 514/519; 514/534; 558/414; 558/428; 558/429; 560/45; 564/133; 564/142; 564/188
[58] Field of Search .................. 564/188, 133, 564/142; 514/623, 519, 531, 530, 534; 558/428, 429, 414; 560/45

[56] References Cited

U.S. PATENT DOCUMENTS 4,710,518 12/1987 Kurahashi et al. .
5,061,731 10/1991 Kurahashi et al. .
5,534,653 7/1996 Wagner et al. .

OTHER PUBLICATIONS

RN 13869–11–9, 1990.
Fugita et al, Chem. Pharm. Bull., 28(2), 453–458, 1980.
Beilstein Reg No. 2013046, 1989.
Beilstein Reg. No. 2757590, 1989.
Beilstein Reg. No. 6059174, 1993.
Beilstein Reg. No. 2853311, 1989.
Beilstein Reg No. 5091636, 1992.
Beilstein Reg. No. 2981433, 1989.
Abstract WO/95/31432, PCT Gazette, Sec.I, 18959, No. 50, 1995.
Abstract, JP 2 233 654, Caplus 1996, p. 12.

*Primary Examiner*—Shailendra Kumar
*Attorney, Agent, or Firm*—Keil & Weinkauf

[57] ABSTRACT

Carboxamides of the formula I $$R^1-\underset{\underset{}{\|}}{C}-N-\underset{\underset{R^4}{|}}{\overset{R^2}{|}}\overset{R^3}{\underset{|}{C}}-Ar \quad (I)$$

where the substituents have the following meanings:

$R^1$ is unsubstituted or substituted bicycloalkyl, tricycloalkyl or bicycloalkenyl;

$R^2, R^3$ and $R^4$ are each, independently of one another, hydrogen, or unsubstituted or substituted: alkyl, cycloalkyl, cycloalkenyl or heterocyclyl;

Ar is unsubstituted or substituted aryl or hetaryl, but excluding 2-cyano-N-[1-(1-naphthyl)ethyl]-3-phenyl-bicyclo[2.2.1]hept-5-ene-2-carboxamide, a process for their preparation, compositions comprising compounds I and the use of compounds I for preparing the compositions, and further a process for controlling harmful fungi and the use of the compounds I for this purpose.

19 Claims, No Drawings

FUNGICIDALLY ACTIVE CARBOXYLIC ACID AMIDES

This application is a 371 of PCT/EP97/01161, filed Mar. 7, 1997.

The present invention relates to carboxamides of the formula I

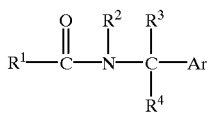

(I)

where the substituents have the following meanings:

R$^1$ is $C_6$–$C_{15}$-bicycloalkyl, $C_6$–$C_{15}$-tricycloalkyl or $C_7$–$C_{15}$-bicycloalkenyl, it being possible for these radicals to be partially or fully halogenated and/or, if they are not fully halogenated, to carry one or, independently of one another, two, three, four or five of the following groups: cyano, $C_1$–$C_4$-alkyl, $C_1$–$C_4$-haloalkyl, $C_1$–$C_4$-alkoxy, $C_1$–$C_4$-haloalkoxy and aryl, it being possible for the aryl to be partially or fully halogenated and/or to carry one or, independently of one another, two or three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

R$^2$,R$^3$,R$^4$ are each, independently of one another, hydrogen, $C_1$–$C_8$-alkyl, which may be partially or fully halogenated and/or carry one or two of the following groups: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl, it being possible for the cyclic groups for their part, to carry one or, independently of one another, two or three halogens, $C_1$–$C_3$-alkyl groups and/or $C_1$–$C_3$-alkoxy groups, and aryl, it being possible for the aryl to be partially or fully halogenated and/or to carry one or, independently of one another, two or three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio or $C_3$–$C_6$-cycloalkyl, $C_3$–$C_6$-cycloalkenyl or heterocyclyl, it being possible for these radicals to be partially or fully halogenated and/or to carry one or, independently of one another, two or three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio;

Ar is aryl or hetaryl, it being possible for these radicals to carry one or, independently of one another, two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl, it being possible for the rings in these groups, for their part, to carry one or, independently of one another, two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, but excluding 2-cyano-N-[1-(1-naphthyl)ethyl]-3-phenylbicydclo[2.2.1]hept-5-ene-2-carboxamide.

The invention additionally relates to a process for preparing the compounds I, to compositions comprising the compounds I and to the use of the compounds I for preparing the compositions.

Furthermore, the invention relates to a process for controlling harmful fungi and to the use of the compounds I for this purpose.

JP-A 02/233 654, EP-A 170 842 and WO-A 95/31432 disclose fungicidal benzylamides. EP-A 653 418 discloses fungicidal amides of bicyclic carboxylic acids.

A paper on asymmetric Diels-Alder reactions also discloses some isomers of 2-cyano-N-[1-(1-naphthyl)ethyl]-3-phenylbicyclo[2.2.1]hept-5-ene-2-carboxamide (J. Org. Chem. 57 (1992), 4664–4669).

However, the compounds from JP-A 02/233 654, EP 170 842 and WO-A 95/31456 are not yet satisfactory with regard to their fungicidal action.

It is an object of the present invention to provide novel carboxamides with improved action against harmful fungi.

We have found that this object is achieved by the compounds I defined above.

Furthermore, the invention provides a process for preparing the compounds I, compositions comprising the compounds I and the use of the compounds I for preparing the compositions and also a process for controlling harmful fungi and the use of the compounds I for this purpose.

The compounds I can be prepared starting from the respective carboxylic acids IIIa

by reaction with amines II (the literature references "Houben-Weyl" refer to: Houben-Weyl, Methoden der Organischen Chemie, 4th edition, Thieme Verlag, Stuttgart).

The carboxylic acids IIIa are known from EP-A 653 418.

The amines II are also generally known or obtainable by known methods (cf. WO-A 95/23 784).

Preferably, the carboxylic acids IIIa are first converted into carboxyl-activated derivatives III, especially into acyl halides—for example chlorides—, acyl cyanides or anhydrides (cf. Tetrahedron Letters 18, 1595–1598 (1973) and "Houben-Weyl", Volume 15/1, p.28 to p. 32). These derivatives III are then reacted with the amines II in the presence of bases.

A suitable way of preparing the acyl cyanides is for example the reaction of the carboxylic acids IIIa with diethyl cyanophosphonate, especially in an inert solvent such as tetrahydrofuran, toluene or dichloromethane.

For preparing the carboxyl-activated anhydrides, preference is given to reacting the carboxylic acids IIIa with chloroformates such as iso-butyl chloroformate in the presence of bases and, if appropriate, in an inert solvent such as toluene or tetrahydrofuran.

The reaction of the amines II with the carboxyl-activated carboxylic acids III is preferably carried out in a solvent such as dichloromethane, tetrahydrofuran or toluene.

Suitable bases are in particular the amines II themselves, and they are usually recovered from the crude product.

In a preferred embodiment of this process step, the carboxylic acid IIIa, the amine II, the reagent suitable for forming the carboxyl-activated derivative of the carboxylic acid III and the base are reacted in a one-pot process, in the presence or absence of an inert solvent.

The thus-obtained reaction mixture is worked up in a conventional manner to give the compounds I, for example by mixing with water, separation of the phases and, if necessary, chromatographic purification of the crude products. Some of the end products are obtained in the form of colorless or slightly brownish, viscous oils which can be freed of volatile particles under reduced pressure and at slightly elevated temperature. If the end products are obtained as solids, purification can also be carried out for example by recrystallization or digestion.

Depending on the kind of substituents, the compounds of the formula I may or may not be obtained as geometrical and/or optical isomers or mixtures of isomers. In particular, in the compounds I, the carbon carrying the groups $R^3$ and $R^4$ may be of R or S configuration according to IUPAC nomenclature. Both the pure isomers described here and the mixtures of isomers have fungicidal activity.

With respect to the radical $R^1$, the remaining part of the molecule in the compounds I may be exo or endo. The two isomers and their mixtures with each other are fungicidally active.

In the definition of the compounds I given above, collective terms were used in general to represent the following substituents:

The statement "partially or fully halogenated" means that some or all of the hydrogens in the thus-characterized groups may be replaced by identical or different halogens as mentioned above.

bicycloalkyl: bicyclic alkyl groups having 6 to 15 carbon ring members, for example bicyclo[2.1.1]hex-5-yl, bicyclo[2.2.1]hept-2-yl, bicyclo[2.2.2]oct-2-yl, bicyclo [3.2.1]oct-6-yl, bicyclo-[3.2.2]non-6-yl, bicyclo[4.2.2] dec-7-yl, bicyclo[3.1.0]hex-1-yl, bicyclo[4.1.0]hept-1-yl, bicyclo[4.3.0]non-1-yl, bicyclo-[4.4.0]dec-1-yl, especially 5-methylbicyclo[2.1.1]hex-5-yl, 2-methylbicyclo[2.2.1]hept-2-yl, 2-methylbicyclo [2.2.2]oct-2-yl, 6-methylbicyclo[3.2.1]oct-6-yl, 6-methylbicyclo[3.2.2]non-6-yl, 7-methylbicyclo [4.2.2]dec-7-yl, 1-methylbicyclo[3.1.0]hex-1-yl, 1-methylbicyclo[4.1.0]hept-1-yl, 1-methylbicyclo [4.3.0]non-1-yl, 1-methylbicyclo[4.4.0]dec-1-yl, 2-methylbicyclo[3.1.0]hex-1-yl, 2-methylbicyclo [4.1.0]hept-1-yl, 2-methylbicyclo[4.3.0]non-1-yl, 2-methylbicyclo[4.4.0]dec-1-yl; tricycloalkyl: tricyclo [3.3.1.1$^{3,7}$]decane (adamantyl), tricyclo[5.2.1.0$^{2,6}$] decane;

Bicycloalkenyl: bicyclic alkenyl groups having 7 to 15 carbon ring members, for example bicyclo[2.2.1]hept-2-en-5-yl, bicyclo-[2.2.2]oct-2-en-5-yl, bicyclo[4.2.2] dec-7-en-2-yl, bicyclo-[4.3.0]non-7-en-1-yl, bicyclo [4.4.0]dec-3-en-1-yl, bicyclo-[4.1.0]hept-3-en-1-yl, 5-methylbicyclo[2.2.1]hept-2-en-5-yl, 5-methylbicyclo [2.2.2]oct-2-en-5-yl, 2-methylbicyclo-[4.2.2]dec-7-en-2-yl, 2-methylbicyclo[4.3.0]non-7-en-1-yl, 2-methylbicyclo[4.4.0]dec-3-en-1-yl, 2-methylbicyclo-[4.1.0]hept-3-en-1-yl;

Halogen: fluorine, chlorine, bromine and iodine;

Alkyl: straight-chain or branched alkyl groups having 1 to 8 carbons, for example $C_1$–$C_6$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylidene: straight-chain or branched alkylidene groups having 3 to 5 carbons, for example 1,3-propylidene, 1,4-butylidene, 1-methyl-1,3-propylidene, 2-methyl-1, 3-propylidene, 2,2-dimethyl-1,3-propylidene, 1,5-pentylidene, 1-methyl-1,4-butylidene;

Haloalkyl or partially or fully halogenated alkyl: straight-chain or branched alkyl groups having 1 to 4 or 8 carbons respectively (as mentioned above), it being possible for the hydrogens in these groups to be partially or fully replaced by halogens (as mentioned above), for example $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkoxy groups having 1 to 4 carbons, for example $C_1$–$C_3$-alkoxy such as methyloxy, ethyloxy, propyloxy and 1-methylethyloxy;

Alkoxyalkyl: straight-chain or branched alkyl groups having 1 to 8 carbons (as mentioned above), carrying in any position a straight-chain or branched alkoxy group (as mentioned above) having in the case of $C_1$–$C_4$-alkoxyalkyl 1 to 4 carbons, such as methoxymethyl, ethoxymethyl, n-propoxymethyl, n-butoxymethyl, 1-methoxyethyl, 2-methoxyethyl, 1-ethoxyethyl, 2-ethoxyethyl, 2-n-propoxyethyl and 2-butoxyethyl;

Haloalkoxy: straight-chain or branched alkoxy groups having 1 to 4 carbons (as mentioned above), it being possible for the hydrogens in these groups to be partially or fully replaced by halogens (as mentioned above), for example $C_1$–$C_2$-haloalkoxy such as chloromethyloxy, dichloromethyloxy, trichloromethyloxy, fluoromethyloxy, difluoromethyloxy, trifluoromethyloxy, chlorofluoromethyloxy, dichlorofluoromethyloxy, chlorodifluoromethyloxy, 1-fluoroethyloxy, 2-fluoroethyloxy, 2,2-difluoroethyloxy, 2,2,2-trifluoroethyloxy, 2-chloro-2-fluoroethyloxy, 2-chloro-2,2-difluoroethyloxy, 2,2-dichloro-2-fluoroethyloxy, 2,2,2-trichloroethyloxy and pentafluoroethyloxy;

Alkylthio: straight-chain or branched alkyl groups having 1 to 4 carbons (as mentioned above), which are attached to the skeleton via a sulfur (—S—), for example $C_1$–$C_4$-alkylthio such as methylthio, ethylthio, propylthio, 1-methylethylthio, n-butylthio and tert-butylthio;

Alkoxycarbonyl: straight-chain or branched alkoxy groups having 1 to 4 carbons (as mentioned above), which are attached to the skeleton via a carbonyl group (—CO—);

Alkenyl: straight-chain or branched alkenyl groups having 2 to 8 carbons and a double bond in any position, for example $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 2-methyl-1-propenyl, 1-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl- 3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched alkynyl groups having 2 to 8 carbons and a triple bond in any position, for example $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Cycloalkyl: monocyclic alkyl groups having 3 to 7 carbons, for example $C_3$–$C_7$-cycloalkyl such as cyclopropyl, cyclobutyl, cyclopentyl, cyclohexyl and cycloheptyl;

Cycloalkenyl: monocyclic alkyl groups having 5 to 7 carbon ring members which contain one or more double bonds, for example $C_5$–$C_7$-cycloalkenyl such as cyclopentenyl, cyclohexenyl and cycloheptenyl;

Heterocyclyl: three- to six-membered, saturated or partially unsaturated mono- or polycyclic heterocycles containing one to three heteroatoms selected from a group consisting of oxygen, nitrogen and sulfur, which are attached to the skeleton, for example 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-diydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydroyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydrohimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, Aryl: monocyclic or polycyclic aromatic groups having 6 to 10 carbons, such as phenyl and naphthyl;

Arylalkyl: aryl groups (as mentioned above) which are in the case of aryl-($C_1$–$C_4$)-alkyl attached to the skeleton via alkyl groups having 1 to 4 carbons (as mentioned above), for example phenyl-($C_1$–$C_4$)-alkyl such as benzyl, 2-phenylethyl, 3-phenylpropyl, 4-phenylbutyl, 1-phenylethyl, 1-phenylpropyl and 1-phenylbutyl;

Aryloxy: aryl groups (as mentioned above), which are attached to the skeleton via an oxygen (—O—), such as phenoxy, 1-naphthoxy and 2-naphthoxy;

Hetaryl: aromatic mono- or polycyclic radicals which may, in addition to carbon ring members, also contain 1 to 4 nitrogen, or 1 to 3 nitrogen and one oxygen or one sulfur, or one oxygen or one sulfur, for example:

5-membered hetaryl containing 1 to 3 nitrogens: 5-membered ring hetaryl groups which may, in addition to carbons, also contain 1 to 3 nitrogen ring members, for example 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing 1 to 4 nitrogens, or 1 to 3 nitrogens and 1 sulfur or oxygen, or 1 oxygen or 1 sulfur: 5-membered ring hetaryl groups which may, in addition to carbons, also contain 1 to 4 nitrogens, or 1 to 3 nitrogens and 1 sulfur or oxygen, or 1 oxygen or sulfur as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol- 3-yl, 1,3,4-oxadiazol-2-yl, 1,3,4-thiadiazol-2-yl, 1,3,4-triazol-2-yl;

benzofused 5-membered hetaryl containing 1 to 3 nitrogens, or 1 nitrogen and/or one oxygen or sulfur: 5-membered ring hetaryl groups, which may, in addition to carbons, also contain 1 to 4 nitrogens, or 1 to 3 nitrogens and 1 sulfur or oxygen, or 1 oxygen or one sulfur ring member, and in which 2 neighboring carbon ring members or 1 nitrogen and 1 neighboring carbon ring member may be bridged by a buta-1,3-diene-1,4-diyl group;

5-membered hetaryl which is attached via nitrogen and contains 1 to 4 nitrogens, or benzofused 5-membered hetaryl which is attached via nitrogen and contains 1 to 3 nitrogens: 5-membered ring hetaryl groups which may, in addition to carbons, also contain 1 to 4 nitrogens or 1 to 3 nitrogen ring members, and in which 2 neighboring carbon ring members or one nitrogen and one neighboring carbon ring member may be bridged by a buta-1,3-diene-1,4-diyl group, these rings being attached to the skeleton via one of the nitrogen ring members;

6-membered hetaryl containing 1 to 3 or 1 to 4 nitrogens: 6-membered ring hetaryl groups which may, in addition to carbons, also contain 1 to 3 or 1 to 4 nitrogen ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzofused 6-membered hetaryl containing 1 to 4 nitrogens: 6-membered ring hetaryl groups in which 2 neighboring carbon ring members may be bridged by a buta-1,3-diene-1,4-diyl group, for example quinolyl, isoquinolyl, quinazolinyl and quinoxalinyl.

With regard to their biological action against harmful fungi, preference is given to compounds I in which the carbon carrying the groups $R^3$ and $R^4$ is of R configuration.

Preference is also given to compounds I in which $R^3$ is hydrogen and $R^4$ is $C_1$–$C_4$-alkyl, especially methyl.

Furthermore, preference is given to compounds I in which Ar is unsubstituted phenyl or phenyl which is substituted in particular in the 2-position or in the 2- and 4-position, especially in the 4-position. Preferred only substituents in the 4-position are cyano, preferably methyl and in particular halogen, especially chlorine.

In addition, preference is given to compounds I in which $R^1$ is unsubstituted or substituted bicycloalkyl having 6 to 10 carbons.

Furthermore, preference is given to compounds I in which $R^1$ is unsubstituted or substituted bicycloalkenyl having 7 to 10 carbons.

Particular preference with respect to their use is given to the compounds I listed in the tables below.

TABLE 1

Compounds of the general formula I.1, where the meanings of the combinations of $Z^1$, $Z^2$ and "*" are defined by the rows of Table A

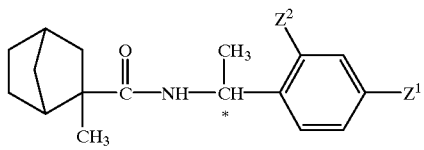

I.1

TABLE 2

Compounds of the general formula I.2, where the meanings of the combinations of $Z^1$, $Z^2$ and "*" are defined by the rows of Table A

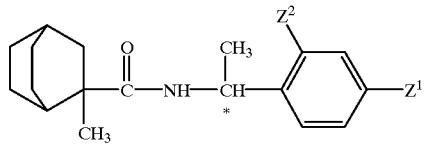

I.2

TABLE 3

Compounds of the general formula I.3, where the meanings of the combinations of $Z^1$, $Z^2$ and "*" are defined by the rows of Table A

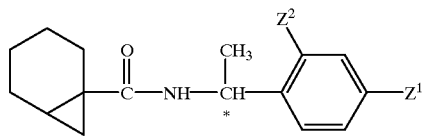

I.3

TABLE 4

Compounds of the general formula I.4, where the meanings of the combinations of $Z^1$, $Z^2$ and "*" are defined by the rows of Table A

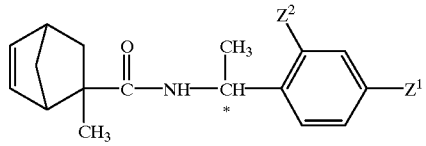

I.4

TABLE 5

Compounds of the general formula I.5, where the meanings of the combinations of $Z^1$, $Z^2$ and "*" are defined by the rows of Table A

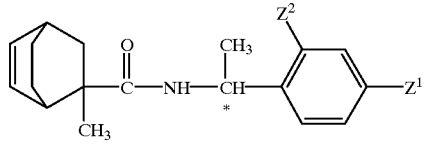

I.5

TABLE 6

Compounds of the general formula I.6, where the meanings of the combinations of $Z^1$, $Z^2$ and "*" are defined by the rows of Table A

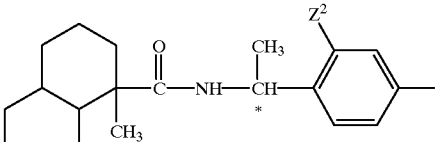

I.6

TABLE 7

Compounds of the general formula I.7, where the meanings of the combinations of $Z^1$, $Z^2$ and "*" are defined by the rows of Table A

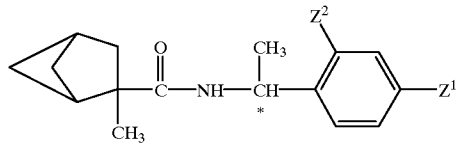
I.7

TABLE 8

Compounds of the general formula I.8, where the meanings of the combinations of $Z^1$, $Z^2$ and "*" are defined by the rows of Table A

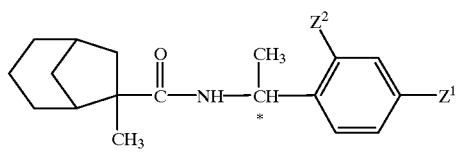
I.8

TABLE 9

Compounds of the general formula I.9, where the meanings of the combinations of $Z^1$, $Z^2$ and "*" are defined by the rows of Table A

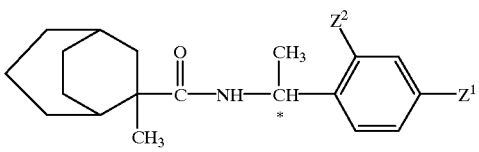
I.9

TABLE 10

Compounds of the general formula I.10, where the meanings of the combinations of $Z^1$, $Z^2$ and "*" are defined by the rows of Table A

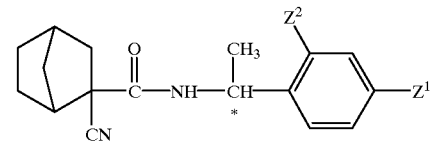
I.10

TABLE 11

Compounds of the general formula I.11, where the meanings of the combinations of $Z^1$, $Z^2$ and "*" are defined by the rows of Table A

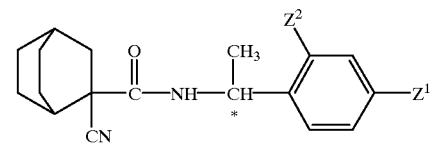
I.11

TABLE 12

Compounds of the general formula I.12, where the meanings of the combinations of $Z^1$, $Z^2$ and "*" are defined by the rows of Table A

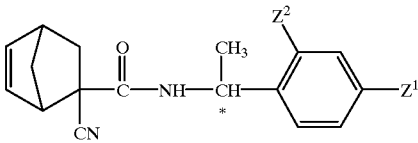
I.12

TABLE 13

Compounds of the general formula I.13, where the meanings of the combinations of $Z^1$, $Z^2$ and "*" are defined by the rows of Table A

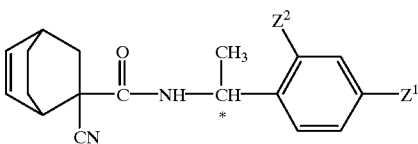
I.13

TABLE 14

Compounds of the general formula I.14, where the meanings of the combinations of $Z^1$, $Z^2$ and "*" are defined by the rows of Table A

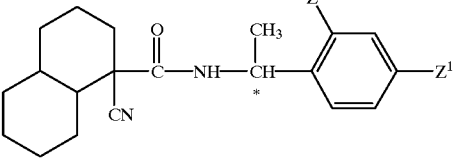
I.14

TABLE 15

Compounds of the general formula I.15, where the meanings of the combinations of $Z^1$, $Z^2$ and "*" are defined by the rows of Table A

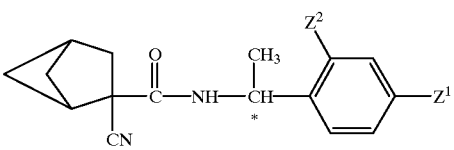
I.15

TABLE 16

Compounds of the general formula I.16, where the meanings of the combinations of $Z^1$, $Z^2$ and "*" are defined by the rows of Table A

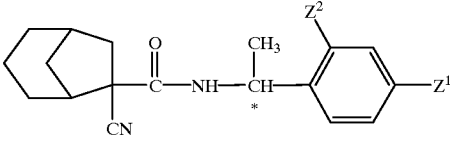
I.16

TABLE 17

Compounds of the general formula I.17, where the meanings of the combinations of $Z^1$, $Z^2$ and "*" are defined by the rows of Table A

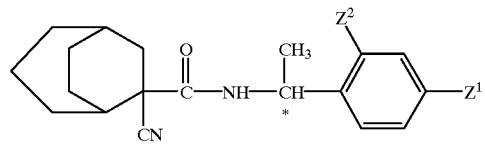
I.17

TABLE 18

Compounds of the general formula I.18, where the meanings of the combinations of $Z^1$, $Z^2$ and "*" are defined by the rows of Table A

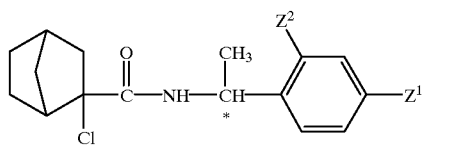
I.18

TABLE 19

Compounds of the general formula I.19, where the meanings of the combinations of $Z^1$, $Z^2$ and "*" are defined by the rows of Table A

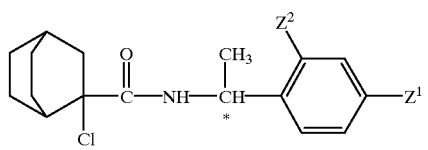
I.19

TABLE 20

Compounds of the general formula I.20, where the meanings of the combinations of $Z^1$, $Z^2$ and "*" are defined by the rows of Table A

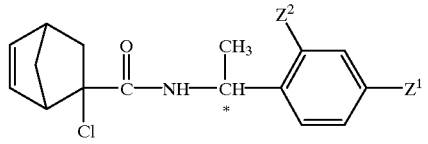
I.20

TABLE 21

Compounds of the general formula I.21, where the meanings of the combinations of $Z^1$, $Z^2$ and "*" are defined by the rows of Table A

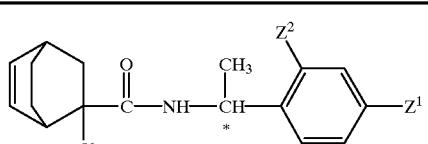
I.21

TABLE 22

Compounds of the general formula I.22, where the meanings of the combinations of $Z^1$, $Z^2$ and "*" are defined by the rows of Table A

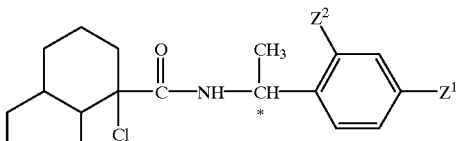
I.22

TABLE 23

Compounds of the general formula I.23, where the meanings of the combinations of $Z^1$, $Z^2$ and "*" are defined by the rows of Table A

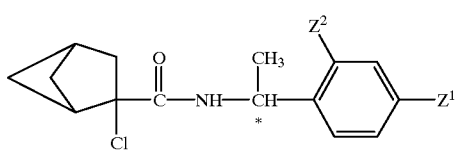
I.23

TABLE 24

Compounds of the general formula I.24, where the meanings of the combinations of $Z^1$, $Z^2$ and "*" are defined by the rows of Table A

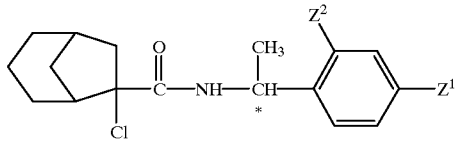
I.24

TABLE 25

Compounds of the general formula I.25, where the meanings of the combinations of $Z^1$, $Z^2$ and "*" are defined by the rows of Table A

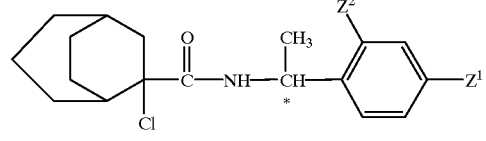
I.25

TABLE 26

Compounds of the general formula I.26, where the meanings of the combinations of $Z^1$, $Z^2$ and "*" are defined by the rows of Table A

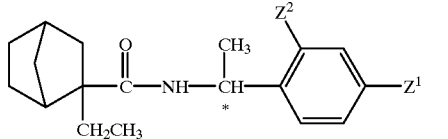
I.26

TABLE 27

Compounds of the general formula I.27, where the meanings of the combinations of $Z^1$, $Z^2$ and "*" are defined by the rows of Table A

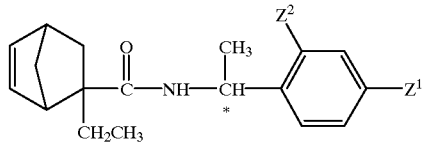
I.27

TABLE 28

Compounds of the general formula I.28, where the meanings of the combinations of $Z^1$, $Z^2$ and "*" are defined by the rows of Table A

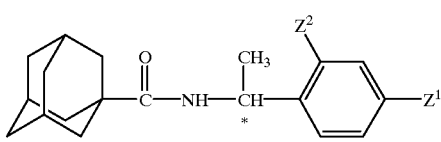
I.28

TABLE 29

Compounds of the general formula I.29, where the meanings of the combinations of $Z^1$, $Z^2$ and "*" are defined by the rows of Table A

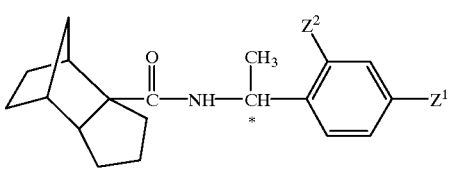
I.29

TABLE A

| No. | $Z^1$ | $Z^2$ | * |
|---|---|---|---|
| 1 | H | H | R |
| 2 | H | H | S |
| 3 | H | H | rac. |
| 4 | H | Cl | R |
| 5 | H | Cl | S |
| 6 | H | Cl | rac. |
| 7 | H | $CH_3$ | R |
| 8 | H | $CH_3$ | S |
| 9 | H | $CH_3$ | rac. |
| 10 | H | $OCH_3$ | R |
| 11 | H | $OCH_3$ | S |
| 12 | H | $OCH_3$ | rac. |
| 13 | H | F | R |
| 14 | H | F | S |
| 15 | H | F | rac. |
| 16 | H | CN | R |
| 17 | H | CN | S |
| 18 | H | CN | rac. |
| 19 | Cl | H | R |
| 20 | Cl | H | S |
| 21 | Cl | H | rac. |
| 22 | Cl | Cl | R |
| 23 | Cl | Cl | S |
| 24 | Cl | Cl | rac. |
| 25 | Cl | $CH_3$ | R |
| 26 | Cl | $CH_3$ | S |
| 27 | Cl | $CH_3$ | rac. |
| 28 | Cl | $OCH_3$ | R |
| 29 | Cl | $OCH_3$ | S |
| 30 | Cl | $OCH_3$ | rac. |
| 31 | Cl | F | R |
| 32 | Cl | F | S |
| 33 | Cl | F | rac. |
| 34 | Cl | CN | R |
| 35 | Cl | CN | S |
| 36 | Cl | CN | rac. |
| 37 | $CH_3$ | H | R |
| 38 | $CH_3$ | H | S |
| 39 | $CH_3$ | H | rac. |
| 40 | $CH_3$ | Cl | R |
| 41 | $CH_3$ | Cl | S |
| 42 | $CH_3$ | Cl | rac. |
| 43 | $CH_3$ | $CH_3$ | R |
| 44 | $CH_3$ | $CH_3$ | S |
| 45 | $CH_3$ | $CH_3$ | rac. |
| 46 | $CH_3$ | $OCH_3$ | R |
| 47 | $CH_3$ | $OCH_3$ | S |
| 48 | $CH_3$ | $OCH_3$ | rac. |
| 49 | $CH_3$ | F | R |
| 50 | $CH_3$ | F | S |
| 51 | $CH_3$ | F | rac. |
| 52 | $CH_3$ | CN | R |
| 53 | $CH_3$ | CN | S |
| 54 | $CH_3$ | CN | rac. |
| 55 | $OCH_3$ | H | R |
| 56 | $OCH_3$ | H | S |
| 57 | $OCH_3$ | H | rac. |
| 58 | $OCH_3$ | Cl | R |
| 59 | $OCH_3$ | Cl | S |
| 60 | $OCH_3$ | Cl | rac. |
| 61 | $OCH_3$ | $CH_3$ | R |
| 62 | $OCH_3$ | $CH_3$ | S |
| 63 | $OCH_3$ | $CH_3$ | rac. |
| 64 | $OCH_3$ | $OCH_3$ | R |
| 65 | $OCH_3$ | $OCH_3$ | S |
| 66 | $OCH_3$ | $OCH_3$ | rac. |
| 67 | $OCH_3$ | F | R |
| 68 | $OCH_3$ | F | S |
| 69 | $OCH_3$ | F | rac. |
| 70 | $OCH_3$ | CN | R |
| 71 | $OCH_3$ | CN | S |
| 72 | $OCH_3$ | CN | rac. |
| 73 | F | H | R |
| 74 | F | H | S |
| 75 | F | H | rac. |
| 76 | F | Cl | R |
| 77 | F | Cl | S |
| 78 | F | Cl | rac. |
| 79 | F | $CH_3$ | R |
| 80 | F | $CH_3$ | S |
| 81 | F | $CH_3$ | rac. |
| 82 | F | $OCH_3$ | R |
| 83 | F | $OCH_3$ | S |
| 84 | F | $OCH_3$ | rac. |
| 85 | F | F | R |
| 86 | F | F | S |
| 87 | F | F | rac. |
| 88 | F | CN | R |
| 89 | F | CN | S |
| 90 | F | CN | rac. |
| 91 | CN | H | R |
| 92 | CN | H | S |
| 93 | CN | H | rac. |
| 94 | CN | Cl | R |
| 95 | CN | Cl | S |
| 96 | CN | Cl | rac. |
| 97 | CN | $CH_3$ | R |
| 98 | CN | $CH_3$ | S |
| 99 | CN | $CH_3$ | rac. |
| 100 | CN | $OCH_3$ | R |
| 101 | CN | $OCH_3$ | S |
| 102 | CN | $OCH_3$ | rac. |
| 103 | CN | F | R |
| 104 | CN | F | S |
| 105 | CN | F | rac. |

TABLE A-continued

| No. | Z¹ | Z² | * |
|-----|----|----|---|
| 106 | CN | CN | R |
| 107 | CN | CN | S |
| 108 | CN | CN | rac. |

(* = Configuration of the individual atom respectively marked "*" in the formulae I.1 to I.29; R = R-configuration; S = S-configuration; rac. = racemic)

The novel compounds I are suitable for controlling harmful fungi.

Depending on their chemical and physical properties, they may be formulated with conventional formulation auxiliaries, i.e. formulation auxiliaries known to a person skilled in the art. The thus-prepared products are called "compositions".

Suitable formulation auxiliaires are, for example, solid or liquid carriers, surfactants and tackifiers.

Liquid carriers are liquid solvents such as water and organic solvents, the latter, especially when using water as solvent, acting as auxiliary solvents. Suitable organic solvents are: aromatics, such as xylene, toluene and alkylnaphthalenes, chlorinated aromatics or chlorinated aliphatic hydrocarbons, such as chlorobenzenes, chloroethylenes and methylene chloride, aliphatic hydrocarbons, such as cyclohexane and paraffins, for example petroleum fractions, alcohols, such as butanol, iso-butanol, cyclohexanol and glycol and also the corresponding ethers and esters, ketones, such as acetone, methyl ethyl ketone, methyl isobutyl ketone and cyclohexanone, and aprotic dipolar solvents, such as dimethylformamide, N-methyl-2-pyrrolidone and dimethyl sulfoxide.

Suitable solid carriers are, for example: ground natural minerals and mineral earths such as silicas, silicates, kaolins, clays, bole, loess, talc, chalk, limestone, lime, dolomite, magnesium oxide, quartz, attapulgite, montmorillonite and diatomaceous earth; ground synthetic materials such as highly disperse silica, ground synthetic aluminum oxide or ground synthetic silicates. Solid carriers particularly suitable for granules are, for example: crushed and fractionated natural rocks, such as calcite, marble, pumice and sepiolite; synthetic granules of inorganic and organic meals; granules of organic material such as sawdust, coconut shells, maize cobs or tobacco stalks.

Suitable surfactants are non-ionic and anionic emulsifiers/foam-formers and dispersants:

polyoxyethylene fatty acid esters, such as lauryl alcohol polyoxyethylene ether acetate, polyoxyethylene alkyl ethers or polyoxypropylene alkyl ethers, for example of iso-tridecylalcohol, and polyoxyethylene fatty alcohol ethers, alkylaryl alcohol polyoxyethylene ethers, such as octylphenyl polyoxyethylene ether tributylphenyl polyoxyethylene ether ethoxylated iso-octyl-, octyl- or nonylphenol or castor oil, sorbitol esters, arylsulfonic acids, alkylsulfonic acids, alkylsulfuric acids, alkali metal salts, alkaline earth metal salts and ammonium salts of arylsulfonic acids, e.g. ligno-, phenol-, naphthalene- and dibutylnaphthalenesulfonic acid, of alkylsulfonic acids, alkylarylsulfonic acids, alkyl, lauryl ether and fatty alcohol sulfates, fatty acids, sulfated hexa-, hepta- and octadecanols and fatty alcohol glycol ethers, condensates of sulfonated naphthalene and its derivatives with formaldehyde, condensates of naphthalenesulfonic acids with phenol or formaldehyde protein hydrolysates and in particular as dispersants: lignin-sulfite waste liquors and methylcellulose.

Suitable tackifiers are, for example: carboxymethylcellulose; natural and synthetic polymers in the form of powders, granules or latices such as gum arabic, polyvinyl alcohol and polyvinyl acetate, natural phospholipids such as cephalins and lecithins, synthetic phospholipids.

Furthermore, the compositions may comprise one or more examples of the following groups of compounds: colorants, other known active compounds, trace nutrients and other additives.

Suitable colorants are, for example, inorganic pigments, such as iron oxide, titanium oxide, Prussian Blue, furthermore organic dyestuffs, such as alizarin dyestuffs, azo dyestuffs and metal phthalocyanine dyestuffs. Other known active compounds are, for example, other fungicides, and also insecticides, acaricides, herbicides and growth-regulators. Trace nutrients are, for example, salts of iron, manganese, boron, copper, cobalt, molybdenum and zinc. Further suitable additives are, for example, mineral and vegetable oils.

In addition, the compositions may be mixed with other mixing partners of practical importance, such as fertilizers and other ready-to-use active compound compositions.

The compositions are prepared in a manner known per se, i.e. depending on the chemical and physical properties of the compounds used, for example by mixing, joint grinding, spraying on, extrusion, granulation, or dissolution in water, the latter, if necessary, with the aid of an organic solvent. Powders, granules and dusts can be obtained for example by mixing or grinding the compounds I together with a solid carrier.

Depending on the compounds used, the compositions are, for example, solutions, emulsions, suspensions, powders, foams, pastes, granules, aerosols or microencapsulations in polymeric substances or in coatings for seeds.

For application, the compositions, which are usually commercially available as concentrates, are, if necessary, dissolved, diluted etc. as is common practice, in the case of spray powders, water-dispersible granules, emulsifiable concentrates, dispersions and also in the case of some microgranules normally by using water. Dusts, granules and spray-solutions are usually not diluted any further with other inert substances prior to application.

The compositions are applied in a manner known per se, for example by spraying, atomizing, dusting, scattering or wetting. Generally, the plants are sprayed or dusted with the compositions. Alternatively or additionally, the seeds of the plants are treated in a manner known per se.

Examples of such preparations are 1. a solution of 90 parts by weight of a compound I according to the invention and 10 parts by weight of N-methyl-2-pyrrolidone, which is suitable for use in the form of microdrops;

2. a mixture of 20 parts by weight of a compound I according to the invention, 80 parts by weight of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil: a dispersion is obtained by finely distributing the solution in water;

3. an aqueous disperson of 20 parts by weight of a compound I according to the invention, 40 parts by weight of cyclohexanone, 30 parts by weight of isobutanol, 20 parts by weight of the adduct of 40 mol of ethylene oxide to 1 mol of castor oil;

4. an aqueous dispersion of 20 parts by weight of a compound I according to the invention, 25 parts by weight of cyclohexanol, 65 parts by weight of a mineral oil fraction of boiling point 210 to 280° C. and 10 parts by weight of the adduct of 40 mol of ethylene oxide to 1 mol of castor oil;

5. a mixture, ground in a hammer mill, of 80 parts by weight of a compound I according to the invention, 3 parts by weight of sodium diisobutylnaphthalene-1-sulfonate, 10 parts by weight of the sodium salt of a lignosulfonic acid from a sulfite waste liquor and 7 parts by weight of pulverulent silica gel: a spray mixture is obtained by finely distributing the mixture in water;

6. an intimate mixture of 3 parts by weight of a compound I according to the invention and 97 parts by weight of finely divided kaolin; this dust comprises 3% by weight of active ingredient;

7. an intimate mixture of 30 parts by weight of a compound I according to the invention, 92 parts by weight of pulverulent silica gel and 8 parts by weight of paraffin oil which has been sprayed onto the surface of this silica gel; this formulation imparts good adhesion to the active ingredient;

8. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, it being possible for this dispersion to be diluted further;

9. a stable oily dispersion of 20 parts by weight of a compound I according to the invention, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 68 parts by weight of a paraffinic mineral oil.

If the compounds I are applied as such, a fine distribution is essential.

The compounds I and the compositions according to the invention are distinguished by an outstanding activity against a broad spectrum of phytopathogenic fungi, in particular from the classes of the Ascomycetes, Basidiomycetes, Deuteromycetes and Phycomycetes.

Some of them act systemically and can be employed as foliar- and soil-acting fungicides.

They are especially important for controlling a large number of fungi in a variety of crop plants, such as wheat, rye, barley, oats, rice, maize, lawns, cotton, soy, coffee, sugar cane, grapevines, fruit species, ornamentals and vegetable species such as cucumbers, beans and cucurbits as well as the seeds of these plants.

The compounds I and the compositions according to the invention are applied by treating the fungi, their habitat, or the seeds, plants, areas, materials or the rooms to be protected against fungal infection, with a fungicidally active amount of the compositions or of the compounds I. Application is effected before or after infection by the fungi.

Specifically, the compositions according to the invention and the compounds I are suitable for controlling the following plant diseases:

*Erysiphe graminis* (powdery mildew) in cereals, *Erysiphe cichoracearum* and *Sphaerotheca fuliginea* in cucurbits, *Podosphaera leucotricha* in apples, *Uncinula necator* in grape vines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, grapevines, ornamentals and vegetables, *Cercospora arachidicola* in groundnuts, *Pseudo-cercosporella herpotrichoides* in wheat, barley, *Pyricularia oryzae* in rice, Phytophthora infestans in potatoes and tomatoes, Fusarium and Verticillium species in a variety of plants, *Plasmopara viticola* in grape vines Pseudoperonospora species in hops and cucumbers and Alternaria species in vegetables and fruit. The compositions according to the invention and the compounds I are preferably used for controlling Botrytis.

The novel compositions or the compounds I can also be employed in the protection of materials (protection of wood), e.g. against Paecilomyces variotii.

In general, the compositions according to the invention comprise from 0.1 to 95, preferably from 0.5 to 90, % by weight of compounds I.

Depending on the nature of the desired effect, the rates of application are from 0.01 to 2.0 kg of compounds I per ha.

In the treatment of seed, amounts of from 0.001 to 50, preferably 0.01 to 10 g of a compound I are generally required per kilogram of seed.

In the compositions according to the invention, the compounds I may also be present together with other active ingredients used in crop protection, e.g. with herbicides, insecticides, growth regulators, fungicides or else with fertilizers. In many cases, a mixture with other fungicides results in a widened fungicidal spectrum of action.

The following list of fungicides together with which the compounds I can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediamine-bis-dithiocarbamate, tetramethylthiuram disulfide, ammonia complex of zinc (N,N'-ethylene-bis-dithiocarbamate), ammonia complex of zinc (N,N'-propylene-bis-dithiocarbamate), zinc (N,N'-propylenebisdithiocarbamate), N,N'-polypropylenebis (thiocarbamoyl)disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diylbis-(1-(2,2,2-trichloroethyl) formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazole-1-ethanol, 1-[3-(2-chlorophenyl)-1-(4-fluorophenyl)oxiran-2-ylmethyl]-1H-1,2,4-triazole, and a variety of fungicides, such as dodecylguanidine acetate, 3-[3-(3,5-dimethyl-2-oxycyclohexyl)-2-hydroxyethyl] glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl) alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl) methylsilyl)methyl)-1H-1,2,4-triazole, strobilurins, such as methyl E-methoximino-[α-(o-tolyloxy)-o-tolyl]acetate, methyl E-2-{2-[6-(2-cyanophenoxy) pyridimin-4-yl-oxy]phenyl}-3-methoxyacrylate, N-methyl-E-methoximino-[α-(2-phenoxyphenyl)] acetamide, N-methyl-E-methoximino-[α-(2,5-dimethyloxy)-o-tolyl]acetamide.

Anilinopyrimidines, such as N-(4,6-dimethylpyrimidin-2-yl)aniline, N-[4-methyl-6-(1-propinyl)pyrimidin-2-yl] aniline, N-(4-methyl-6-cyclopropylpyrimidin-2-yl)aniline.

Phenylpyrroles, such as 4-(2,2-difluoro-1,3-benzodioxol-4-yl)pyrrole-3-carbonitrile.

Cinnamamides, such as 3-(4-chlorophenyl)-3-(3,4-dimethoxyphenyl)acryloylmorpholine.

(2RS,3SR)-1-[3-(2-chlorophenyl)-2-[4-fluorophenyl] oxiran-2-ylmethyl]-1H-1,2,4-triazole.

PREPARATION EXAMPLES

EXAMPLE 1

2-Methyl-bicyclo[2.2.1]hept-5-ene-2-[N-(1-(p-chlorophenyl)ethyl)]carboxamide

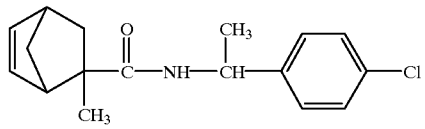

The solution of 0.53 g (3.46 mmol) of 2-methylbicyclo [2.2.1]hept-5-ene-2-carboxylic acid and 0.54 g (3.46 mmol) of racemic 1-amino-1-(p-chlorophenyl)ethane in 50 ml of dichloromethane was admixed with 0.56 g (3.46 mmol) of diethyl cyanophosphonate and 0.77 g (7.61 mmol) of triethylamine at 0° C. Cooling with ice, stirring was continued for 1 hour and then, at 20° C., for 15 hours. Subsequently, the solution was washed in succession with the same volume of 2N sodium hydroxide solution, water, 10% strength hydrochloric acid and again water, dried and concentrated. 0.8 g (2.76 mmol) of the title compound (M.p. 118–22° C., Compound 1.7 in Table E1) were obtained.

The procedures of the preparation example above may be employed to prepare further representatives of the compounds I by modifying the starting materials. The physical data of the products prepared in this way are listed in the following tables.

TABLE E1

| No. | Z | # | * | Fp. (° C.) |
|---|---|---|---|---|
| 1.1 | 4-CH₃ | endo | rac. | 125–30 |
| 1.2 | 4-CH₃ | exo | rac. | 125–30 |
| 1.3 | 4-CH₃ | exo | R | 140–5 |
| 1.4 | 4-CH₃ | endo | R | 133–8 |
| 1.5 | 4-OCH₃ | exo | rac. | 120–2 |
| 1.6 | 4-OCH₃ | endo | rac. | 105–10 |
| 1.7 | 4-Cl | mixture | rac. | 118–22 |
| 1.8 | 4-CN | mixture | rac. | 110–12 |
| 1.9 | 4-Cl | exo | R | 126–30 |
| 1.10 | 4-Cl | endo | R | 124–8 |
| 1.11 | 4-Cl | mixture | S | 120–4 |
| 1.12 | 2,4-(CH₃)₂ | mixture | rac. | 140–5 |
| 1.13 | 2,4-(Cl)₂ | mixture | rac. | 150–5 |

TABLE E2

[Structure: norbornene with C(CN)(#)-C(=O)-NH-CH(CH3)(*)-phenyl-Z]

| No. | Z | # | * | Fp. (° C.) |
|---|---|---|---|---|
| 2.1 | 4-CN | exo | rac. | 133–5 |
| 2.2 | 4-CN | endo | rac. | 118–21 |
| 2.3 | 4-CH₃ | exo | rac. | 87–91 |
| 2.4 | 4-CH₃ | endo | rac. | 118–20 |
| 2.5 | 4-OCH₃ | exo | rac. | 93–5 |
| 2.6 | 4-OCH₃ | endo | rac. | 112–5 |
| 2.7 | 4-Cl | exo | S | 112–4 |
| 2.8 | 4-Cl | endo | S | 117–20 |
| 2.9 | 4-Cl | exo | R | 117–20 |
| 2.10 | 4-Cl | endo | R | 106–8 |

TABLE E3

[Structure: norbornane with C(CH3)(#)-C(=O)-NH-CH(CH3)(*)-phenyl-Z]

| No. | Z | # | * | Fp. (° C.) |
|---|---|---|---|---|
| 3.1 | 4-CH₃ | mixture | R | 120–5 |
| 3.2 | 4-Cl | mixture | rac. | 120–5 |
| 3.3 | 4-OCH₃ | mixture | rac. | 85–90 |
| 3.4 | 4-OC₆H₅ | mixture | rac. | 85–90 |
| 3.5 | 4-CH₃ | mixture | rac. | 97–103 |
| 3.6 | 4-CN | mixture | rac. | 108–10 |
| 3.7 | 4-Cl | mixture | R | 134–6 |
| 3.8 | 4-Cl | mixture | S | 136–8 |
| 3.9 | 2,4-(CH₃)₂ | mixture | rac. | 145 |
| 3.10 | 2,4-(Cl)₂ | mixture | rac. | 180–2 |

TABLE E4

[Structure: norbornene with C(Cl)(#)-C(=O)-NH-CH(CH3)(*)-phenyl-Z]

| No. | Z | # | * | Fp. (° C.) |
|---|---|---|---|---|
| 4.1 | 4-Cl | mixture | mixture | 83–5 |
| 4.2 | 4-Cl | mixture | R | 98–100 |
| 4.3 | 4-OMe | mixture | rac. | 118–20 |
| 4.4 | 4-Me | mixture | rac. | 90–92 |

TABLE E5

[Structure: bicyclic with C(#)-C(=O)-NH-CH(CH3)(*)-phenyl-Z]

| No. | Z | # | * | Fp. (° C.) |
|---|---|---|---|---|
| 5.1 | 4-Cl | mixture | R | 84–88 |
| 5.2 | 4-OMe | mixture | rac. | 95–98 |
| 5.3 | 4-Cl | mixture | rac. | 144–8 |

TABLE E6

[Structure: adamantyl-C(=O)-NH-CH(CH3)(*)-phenyl-Z]

| No. | Z | * | Fp. (° C.) |
|---|---|---|---|
| 6.1 | 4-Cl | R | 173–5 |
| 6.2 | 4-OMe | rac. | 144–6 |
| 6.3 | 4-Cl | rac. | 175–8 |

Use Examples

The fungicidal activity of the compounds of the general formula I was demonstrated by the following experiments:

The active ingredients were formulated as a 20% strength emulsion in a mixture of 70% by weight of cyclohexanol, 20% by weight of Nekanil® LN (Lutensol® AP6, wetting agent with emulsifier and dispersant action based on ethoxylated alkylphenols) and 10% by weight of Emulphor® EL (Emulan® EL, emulsifier based on ethoxylated fatty alcohols) and diluted with water to give the desired concentration.

Activity against Pyricularia Oryzae

Leaves of rice seedlings (variety: "Tai-Nong 67") grown in pots were sprayed dripping wet with aqueous emulsions containing in the dry substance 80% of active ingredient and 20% of emulsifier.

After 24 hours, the plants were inoculated with an aqueous spore suspension of Pyricularia oryzae. The test plantswere then kept in controlled environment chambers at 22–24° C. under a relative atmospheric humidity of 95–99%. after 6 days, the disease levels were determined.

In this test, the active compounds 1.3, 1.4, 1.7, 1.9, (Table E1) and 3.1 and 3.7 (Table E3) were in each case applied on their own in the form of an aqueous spray mixture having an active compound content of 250 ppm.

At the end of the test, 0 to 5% of the surface of the leaves was infected with Pyricularia oryzae, whereas 70% of the untreated leaves were infected.

We claim:

1. A carboxamide of the formula I

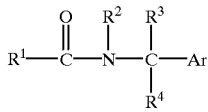

(I)

where the substituents have the following meanings:

$R^1$ is $C_6$–$C_{15}$-bicycloalkyl, tricyclo[3.3.1.1$^{3,7}$]decane, tricyclo[5.2.1.0$^{2,6}$]decane or $C_7$–$C_{15}$-bicycloalkenyl, it being possible for these radicals to be partially or fully halogenated and/or, if they are not fully halogenated, to carry one or, independently of one another, two, three, four or five of the following groups: cyano, $C_1$–$C_4$-alkyl, $C_1$–$C_4$-haloalkyl, $C_1$–$C_4$-alkoxy, $C_1$–$C_4$-haloalkoxy and aryl, it being possible for the aryl to be partially or fully halogenated and/or to carry one or, independently of one another, two or three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^2$ is hydrogen, $R^3$ is hydrogen,

Ar is phenyl, which carries one or, independently of one another, two or three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and hetaryl, it being possible for the rings in these groups, for their part, to carry one or, independently of one another, two or three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, $R^4$ is $C_1$–$C_4$-alkyl, which may be partially or fully halogenated and/or carry one or two of the following groups: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl, it being possible for the cyclic groups, for their part, to carry one or, independently of one another, two or three halogens, $C_1$–$C_3$-alkyl groups and/or $C_1$–$C_3$-alkoxy groups, and aryl, it being possible for the aryl to be partially or fully halogenated and/or to carry one or, independently of one another, two or three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio or $C_3$–$C_6$-cycloalkyl, $C_3$–$C_6$-cycloalkenyl or heterocyclyl, it being possible for these radicals to be partially or fully halogenated and/or to carry one or, independently of one another, two or three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio.

2. A process for preparing the carboxamide I defined in claim 1, which comprises reacting an amine of the formula II

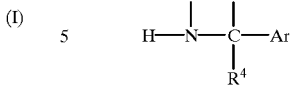

(II)

in the presence of a base with a carboxyl-activated carboxylic acid of the formula III

 (III)

where X is halogen or a leaving group customary in acylation reactions.

3. A composition suitable for controlling harmful fungi, comprising an active amount of the carboxamide I defined in claim 1 and at least one customary formulation auxiliary.

4. A process for controlling harmful fungi, which comprises treating the harmful fungi, their habitat or the plants, areas, materials or spaces to be kept free from said fungi with a fungicidally active amount of the carboxamide I defined in claim 1.

5. A carboxamide of the formula I

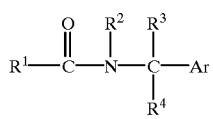

(I)

where the substituents have the following meanings:

$R^1$ is $C_6$–$C_{15}$-bicycloalkyl, tricyclo[3.3.1.1$^{3,7}$]decane, tricyclo[5.2.1.0$^{2,6}$]decane or $C_7$–$C_{15}$bicycloalkenyl, it being possible for these radicals to be partially or fully halogenated and/or, if they are not fully halogenated, to carry one or, independently of one another, two, three, four or five of the following groups: cyano, $C_1$–$C_4$-alkyl, $C_1$–$C_4$-haloalkyl, $C_1$–$C_4$-alkoxy, $C_1$–$C_4$-haloalkoxy and aryl, it being possible for the aryl to be partially or fully halogenated and/or to carry one or, independently of one another, two or three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

$R^2$ is hydrogen, $R^3$ is hydrogen,

Ar is phenyl, which carries a radical $Z^1$ in the 4-position or a radical $Z^2$ in the 2-position, or a radical $Z^1$ in the 4-position and a radical $Z^2$ in the 2-position, and $Z^1$ and $Z^2$ are, independently of one another cyano, halogen or $C_1$–$C_4$-alkyl, and $R^4$ is $C_1$–$C_4$-alkyl, which may be partially or fully halogenated and/or carry one or two of the following groups: $C_1$–$C_4$-alkoxy, $C_1$–$C_4$-haloalkoxy, $C_1$–$C_4$-alkylthio, $C_3$–$C_7$-cycloalkyl, $C_5$–$C_7$-cycloalkenyl, it being possible for the cyclic groups, for their part, to carry one or, independently of one another, two or three halogens, $C_1$–$C_3$-alkyl groups and/or $C_1$–$C_3$-alkoxy groups, and aryl, it being possible for the aryl to be partially or fully halogenated and/or to carry one or, independently of one another, two or three of the following substituents: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio or $C_3$–$C_6$-cycloalkyl, $C_3$–$C_6$-cycloalkenyl or heterocyclyl, it being possible for these radicals to be partially or fully halogenated and/or to carry one or, independently of one another, two or three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio.

6. The carboxamide defined in claim 5, wherein $Z^1$ is halogen.

7. The carboxamide defined in claim 5, wherein $Z^1$ is $C_1$–$C_4$-alkyl.

8. The carboxamide defined in claim 5, wherein $Z^2$ is halogen.

9. The carboxamide defined in claim 5, wherein $Z^2$ is $C_1$–$C_4$-alkyl.

10. The carboxamide defined in claim 5, wherein $R^1$ is $C_6$–$C_{15}$-bicycloalkyl.

11. The carboxamide defined in claim 5, wherein $R^1$ is tricyclo[3.3.1.1]decane or tricyclo[5.2.1.0]decane.

12. The carboxamide defined in claim 5, wherein $R^1$ is a radical

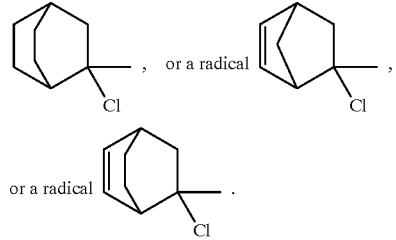

13. The carboxamide defined in claim 5, wherein $Z^1$ or $R^2$ or both are halogen.

14. The carboxamide defined in claim 5, wherein the bi- or tricyclic radical in the position of $R^1$ is partially or fully halogenated.

15. The carboxamide defined in claim 5, wherein the bi- or tricyclic radical in the position of $R^1$ is partially halogenated.

16. The carboxamide defined in claim 5, wherein $R^4$ is $C_1$–$C_6$-alkyl.

17. A process for preparing the carboxamide I defined in claim 5, which comprises reacting an amine of the formula II

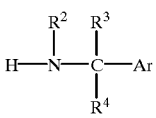 (II)

in the presence of a base with a carboxyl-activated carboxylic acid of the formula III

$R^1$—COX     (III)

where X is halogen or a leaving group customary in acylation reactions.

18. A composition suitable for controlling harmful fungi, comprising an active amount of the carboxamide I defined in claim 5 and at least one customary formulation auxilliary.

19. A process for controlling harmful fungi, which comprises treating the harmful fungi, their habitat or the plants, areas, materials or spaces to be kept free from said fungi with a fungicidally active amount of the carboxamide I defined in claim 5.

* * * * *